(12) United States Patent
Verhaert

(10) Patent No.: US 11,614,450 B2
(45) Date of Patent: Mar. 28, 2023

(54) MASS SPECTROMETRY HISTOCHEMISTRY OF PEPTIDES FROM FORMALDEHYDE-FIXED, PARAFFIN-EMBEDDED TISSUE

(71) Applicant: Peter Dominiek Emiel Maria Verhaert, Vorselaar (BE)

(72) Inventor: Peter Dominiek Emiel Maria Verhaert, Vorselaar (BE)

( * ) Notice: Subject to any disclaimer, the term of this patent is extended or adjusted under 35 U.S.C. 154(b) by 278 days.

(21) Appl. No.: 16/618,504

(22) PCT Filed: Jun. 1, 2018

(86) PCT No.: PCT/EP2018/064408
§ 371 (c)(1),
(2) Date: Dec. 2, 2019

(87) PCT Pub. No.: WO2018/220151
PCT Pub. Date: Dec. 6, 2018

(65) Prior Publication Data
US 2020/0124617 A1 Apr. 23, 2020

(30) Foreign Application Priority Data
Jun. 2, 2017 (EP) .................................... 17174163

(51) Int. Cl.
*G01N 33/68* (2006.01)
*G01N 1/28* (2006.01)

(52) U.S. Cl.
CPC .......... *G01N 33/6851* (2013.01); *G01N 1/28* (2013.01); *G01N 1/286* (2013.01); *G01N 2001/2873* (2013.01); *G01N 2560/00* (2013.01)

(58) Field of Classification Search
CPC .. G01N 1/28; G01N 1/286; G01N 2001/2873; G01N 2560/00; G01N 33/6851
See application file for complete search history.

(56) References Cited

U.S. PATENT DOCUMENTS

| | | | |
|---|---|---|---|
| 8,283,625 B2* | 10/2012 | Sato | H01J 49/164 250/281 |
| 9,700,485 B2* | 7/2017 | Weeks | C07K 16/2875 |
| 9,870,909 B2* | 1/2018 | Trimpin | H01J 49/16 |
| 10,551,383 B2* | 2/2020 | Haack | G01N 33/57484 |
| 11,149,317 B2* | 10/2021 | Van Engeland | C12Q 1/6886 |
| 2007/0138385 A1 | 6/2007 | Kulp et al. | |

(Continued)

OTHER PUBLICATIONS

Cerruti, Christopher D., et al. "MALDI imaging mass spectrometry of lipids by adding lithium salts to the matrix solution." Analytical and bioanalytical chemistry 401.1 (2011): 75-87 (Year: 2011).*

(Continued)

*Primary Examiner* — Wyatt A Stoffa
(74) *Attorney, Agent, or Firm* — Dinsmore & Shohl, LLP

(57) ABSTRACT

The present invention in general relates to a method of localization and structural characterization of peptides in a formaldehyde-fixed paraffin-embedded biological sample using matrix assisted ionization (such as in MALDI). Specifically, the invention relates to the combination of the development of a sample preparation protocol which does not require any enzymatic digestion nor antigen-retrieval steps, with highly sensitive mass spectrometry.

7 Claims, 2 Drawing Sheets

(56) References Cited

U.S. PATENT DOCUMENTS

| | | | |
|---|---|---|---|
| 2010/0038529 A1* | 2/2010 | Sato | G01N 1/2813 250/288 |
| 2010/0285045 A1* | 11/2010 | Saarma | A61P 25/28 514/17.7 |
| 2013/0078253 A1* | 3/2013 | Fang | C07K 14/57 435/235.1 |
| 2015/0369810 A1* | 12/2015 | Haack | C12Q 1/6886 514/266.4 |
| 2020/0363417 A1* | 11/2020 | Haack | A61K 31/4162 |

OTHER PUBLICATIONS

Kakimoto, Yu, et al. "Novel in situ pretreatment method for significantly enhancing the signal in MALDI-TOF MS of formalin-fixed paraffin-embedded tissue sections." (2012): e41607 (Year: 2012).*

Lemaire, R., et al. "Direct analysis and MALDI imaging of formalin-fixed, paraffin-embedded tissue sections." Journal of proteome research 6.4 (2007): 1295-1305 (Year: 2007).*

Calvano, Cosima Damiana, et al. "MALDI matrices for low molecular weight compounds: an endless story?." Analytical and bioanalytical chemistry 410.17 (2018): 4015-4038 (Year: 2018).*

Matthews, et al., "Hyperglycaemia induced by anaesthesia in the american cockroach, *Periplaneta americana* L." Canadian Journal of Zoology, 1973, 51(3), pp. 395-397.

Lemaire, R., et al., "Direct analysis and MALDI Imaging of Formalin-Fixed Paraffin-Embedded Tissue Sections," Journal of Proteome Research 6, 2007, pp. 1295-1305.

Shaw, C. and Verhaert, P.D.E.M., "Peptidomics and Biology: Two Disciplines Driving Each Other," Peptidomics Methods and Applications, John Wiley & Sons: 2007, pp. 389-396.

Chaurand, P., et al., "Imaging mass spectrometry of intact proteins from alcohol-preserved tissue specimens: bypassing formalin fixation," Journal of Proteome Research 7, 2008, pp. 3543-3555.

Wisniewski, J. R., "Proteomic Sample Preparation from Formalin Fixed and Paraffin Embedded Tissue," Journal of Visualized Experiments 79, 2013, pp. 1-5.

Gustafsson, O.J.R., et al., "Proteomic developments in the analysis of formalin-fixed tissue," Biochimica et Biophysica Acta—Proteins and Proteomics 1854, 2015, pp. 559-580.

Quesada-Calvo, F., et al., "Comparison of two FFPE preparation methods using label-free shotgun proteomics: Application to tissues of diverticulitis patients," Journal of Proteomics 112, 2015, pp. 250-261.

Rai, R., et al., "Biosafe substitutes for xylene," International Journal of Information Research and Review, vol. 3, Issue 6, 2016, pp. 2529-2532.

Extended European Search Report dated Nov. 23, 2017 in related European Application No. 17174163.0.

Lu, M., et al., "Nanomaterials as assisted matrix of laser desorption/ionization time-of-flight mass spectrometry for the analysis of small molecules," Nanomaterials 7, 2017, pp. 1-21.

International Search Report and Written Opinion dated Jul. 31, 2018 in related International Application No. PCT/EP2018/064408.

Caprioli, R.J., et al., "Molecular imaging of biological samples: localization of peptides and proteins using MALDI-TOF MS," Anal Chem. 69, 1997, pp. 4751-4760.

Predel, R.; Gaede, G. "Peptidomics of neurohemal organs from species of the cockroach family Blattidae: how do neuropeptides of closely related species differ?" Peptides 26, 2005, pp. 3-9.

Verhaert, P., et al., "A new alternative for simultaneous immunohistochemical screening of 96 hybridoma clones for tissue-specific antibody productions selects a monoclonal antibody to insect corpus cardiacum," Journal of Neuroscience Methods 17, 1986, pp. 261-268.

Verhaert, P.D.E.M., "Imaging of Similar Mass Neuropeptides in Neuronal Tissue by Enhanced Resolution MALDI MS with an Ion Trap—OrbitrapTM Hybrid Instrument," Mass Spectrometry Imaging, Methods in Molecular Biology 656, Humana Press, 2010, pp. 433-449.

Wysocki, et al., "Mass spectrometry of peptides and proteins," Methods 35, 2005, pp. 211-222.

Grey, et al., "Molecular Morphology of the Chick Heart Visulaized by MALDI Imaging Mass Spectrometry," The Anatomical Record: AR; Advances in Integrative Anatomy and Evolutionary Biology, vol. 293, No. 5, 2010, pp. 821-828.

Achim Buck, et al., "High-resolution MALDI-FT_ICR MS imaging for the analysis of metabolites from formalin-fixed, paraffin-embedded clinical tissue samples," The Journal of Pathology, vol. 237, No. 1, 2015, pp. 123-132.

\* cited by examiner

MASS SPECTROMETRY HISTOCHEMISTRY OF PEPTIDES FROM FORMALDEHYDE-FIXED, PARAFFIN-EMBEDDED TISSUE

FIELD OF THE INVENTION

The present invention in general relates to a method of localization and structural characterization of peptides in a formaldehyde-fixed paraffin-embedded biological sample using matrix assisted ionization (such as in MALDI). Specifically, the invention relates to the combination of the development of a sample preparation protocol which does not require any enzymatic digestion nor antigen-retrieval steps, with highly sensitive mass spectrometry.

BACKGROUND TO THE INVENTION

The present invention relates to a method of imaging peptides, especially endogenously produced peptides, such as neuropeptides, in a formaldehyde-fixed, paraffin-embedded biological sample using matrix assisted ionization mass spectrometry (primarily MALDI). The relevance of the detection and characterization of peptides in biological samples has been described extensively in the final chapter of a book entirely devoted to the discipline of *Peptidomics* (Shaw et al., 2007); which concluded the following:

Endogenous (secretory) peptides can be regarded as the vocabulary of intercellular communication and, as such, are pivotal molecules in biology.

They are fundamental to the understanding of physiological processes in all multicellular (and even unicellular) organisms, including human.

Peptides are among the key molecular regulators which either remotely, locally, or indeed in a self-controlled manner, direct cells to respond/not respond, divide/not divide, grow/not grow/die, secrete/not secrete, seal off/open up for extracellular chemicals, move/stay put, and so on.

As these are among the very processes that biomedical life scientists wish to modulate in virtually all disease states, the understanding of the function of the peptidome is absolutely essential to the understanding of many pathologies and in the development of both diagnostics and therapeutics in a rational manner, i.e. via a highly specifically targeted approach, based on the system of internal regulation that has evolved in biological systems over many millions of years.

To fully understand the biological significance of a peptide, knowledge about its tissue distribution is equally important as its primary structure or concentration. It should, therefore, not be surprising that, throughout the years, our excitement for innovative analytical technologies combining tissue localization information of peptides with their chemical identification (and quantitation) has been consistent. Unsurpassed histological localization of peptides (with excellent (sub-micron) spatial resolution) combined with partial chemical characterization is offered by immunohistochemistry. Superior peptide primary structure characterization combined with low to medium spatial resolution is provided by direct tissue mass spectrometry. We have been employing these techniques respectively in the eighties and nineties of the past century.

It is only in the first decade of this century that a reasonable spatial resolution together with high performance mass spectrometry could be combined in the technology designated as mass spectrometry imaging (MSI). We have embraced this technology from its emergence, although it was evident that, particularly secretory, peptides are not the type of analytes that are easily detectable by the original MSI procedures. With the retrocerebral complex of a cockroach (equivalent to the mammalian hypohysis), i.e. its major neurosecretory gland, as carefully selected elegant model system (Verhaert et al., 2010), we have optimized MSI protocols over the past years to the level required in order to enable neuropeptide analysis (see refs. in Verhaert et al., 2010).

The use of enzymatic digestion and antigen-retrieval steps on tissue sections is currently the golden standard for improving protein detection in standard methods for MALDI-MSI (Wiśniewski, 2013; Quesada-Calvo et al., 2015; Gustafsson et al., 2015). Especially when targeting small soluble proteins, like secretory peptides, also during pre-tissue sectioning sample preparation care should be taken to include as few steps as possible which may lead to analyte loss, such as through extraction, proteolytic degradation, or washing out from the tissue sample. Since (snap-)freezing a sample is known to only temporarily inactivate the many katabolic enzymes present in biological samples, and, therefore, risks to result in endogenous peptide loss through enzymatic breakdown, we developed this method for tissue samples fixed by chemical crosslinking like with widely used formaldehyde-based fixatives.

Moreover, since both during the deparaffinization steps as well as in the conventional subsequent enzymatic digestion and antigen-retrieval steps, there is a high chance of extracting and/or washing off small peptides from the sample, thereby losing a lot of crucial information, it was an object of the present invention to provide a method for mass spectrometry imaging of peptides, with a significantly reduced likelihood of removing peptides during the sample preparation steps.

Methods for direct analysis and MALDI imaging of Formalin-Fixed Paraffin-Embedded (FFPE) tissue sections are described in Lemaire et al., 2007. Herein, 2 methods are mentioned. The first approach is reported to be applicable for all FFPE tissues regardless of their preservation time and is based on antigen retrieval steps combined with in situ enzymatic digestion of the tissue section after paraffin removal. For this method many examples are found in the literature. The second method relies on the use of a reactive matrix 2,4-dinitrophenylhydrazine, useful for FFPE tissues, and is reported to work exclusively for samples stored less than 1 year. Hence the current understanding is that formaldehyde fixation is to be avoided when one wants to image peptides by mass spectrometry, without the use of sample treatment to reverse the cross-linking, such as antigen retrieval steps (Chaurand et al., 2008).

Contrary to the general perception in the field, we have found that for imaging of peptides including neuropeptides and other secretory endogenously produced peptides, no enzymatic digestion and/or antigen-retrieval steps are required. In contrast, direct application of a conventional MALDI matrix, such as dihydroxybenzoic acid, after the deparaffinization and drying steps, allows for the detection of such peptides in the sample. Even more interesting, using this newly developed method, we could differentiate tumor sample from normal tissue based on their peptide profile. Until now, this has been very difficult, presumably due to the washing off of differentiating peptides during the processing steps of the samples, below the sensitivity threshold of the overall mass spectrometric peptide detection method. Hence, we herewith also provide a new method for diagnostic imaging as well as peptide biomarker identification, including for disease areas which are at present difficult to diagnose and/or stage.

SUMMARY OF THE INVENTION

In a first aspect, the present invention provides a method for imaging peptides in a paraffin embedded (PE) biological sample; said method comprising the steps of:
a) providing a paraffin embedded (PE) sample;
b) sectioning said sample of step a);
c) deparaffinizing said sectioned sample of step b)
d) air drying said sectioned sample of step c)
e) applying a MALDI (matrix-assisted laser desorption ionization imaging) matrix to said air-dried samples of step d; and
f) performing a mass spectrometry analysis tuned for peptide analytes on said sample of step e).

The method of the present invention is in particular characterized in that it does not comprise an enzymatic digestion step, nor an antigen-retrieval step.

In a preferred embodiment, the present invention provides a method for imaging peptides in a paraffin embedded (PE) biological sample; said method comprising the steps of:
a) providing a formaldehyde-fixed paraffin embedded (PE) sample;
b) sectioning said sample of step a);
c) deparaffinizing said sectioned sample of step b)
d) air drying said sectioned sample of step c)
e) applying a conventional MALDI (matrix-assisted laser desorption ionization imaging) matrix to said air-dried samples of step d; and
f) performing a mass spectrometry analysis tuned for peptide analytes on said sample of step e);
wherein said method does not comprise an enzymatic digestion step, nor an antigen-retrieval step.

In a specific embodiment of the present invention, the deparaffinization step (i.e. step c in the above method) is performed by immersing the (formaldehyde-fixed) PE sample at room temperature one or more times in 100% xylene for about 1-5 min, followed by one or more washing steps in absolute ethanol, each lasting about 1-5 min.

In a more specific embodiment of the present invention, the deparaffinization step (i.e. step c in the above method) is performed by immersing the sectioned samples of step b) at room temperature sequentially in:
100% xylene for about 3 min;
100% xylene for about 2 min;
absolute ethanol for about 2 min; and
absolute ethanol for about 1 min.

In another specific embodiment, the conventional MALDI matrix as applied in step e) of the above method is a MALDI matrix, such as comprising one of the following: sinapinic acid (SA) (e.g. alpha-cyano sinapinic acid); cinnamic acid (e.g. [alpha]-4-cyano hydroxyl cinnamic acid (CHCA)); 2,5-dihydroxybenzoic acid (DHB); 3-hydroxypicolinic acid; dithranol; and derivatives of any of these; in particular DHB. In addition, the MALDI matrix may further comprise an additive to enhance analyte ionization and desorption, such as for example lithium (Li)-salts.

Preferably, the method according to the present invention is performed such that the mass spectrometry analysis is optimally tuned for peptide analytes. Relevant instrumentation and settings are reviewed in the literature, with modern instruments performing with higher mass accuracy and sensitivity than older generation systems (Wysocki et al., 2005).

BRIEF DESCRIPTION OF THE DRAWINGS

With specific reference now to the figure, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
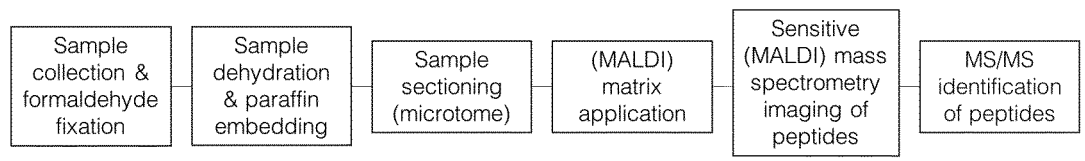
FIG. 1: General procedure and order of steps as used in the method according to the present invention.

In a first aspect, the present invention provides a method for imaging peptides in a paraffin embedded (PE) biological sample; said method comprising the steps of:
a) providing a paraffin embedded (PE) sample;
b) sectioning said sample of step a);
c) deparaffinizing said sectioned sample of step b)
d) air drying said sectioned sample of step c)
e) applying a MALDI (matrix-assisted laser desorption ionization imaging) matrix to said air-dried samples of step d; and
f) performing a mass spectrometry analysis tuned for peptide analytes on said sample of step e).

In a preferred embodiment, the present invention provides a method for imaging peptides in a paraffin embedded (PE) biological sample; said method comprising the steps of:
  a) providing a formaldehyde-fixed paraffin embedded (PE) sample;
  b) sectioning said sample of step a);
  c) deparaffinizing said sectioned sample of step b)
  d) air drying said sectioned sample of step c)
  e) applying a conventional MALDI (matrix-assisted laser desorption ionization imaging) matrix to said air-dried samples of step d; and
  f) performing a mass spectrometry analysis tuned for peptide analytes on said sample of step e);
  wherein said method does not comprise an enzymatic digestion step, nor an antigen-retrieval step.

The term "polypeptide," "peptide," "oligopeptide," or "protein" as used herein refers to any composition that includes two or more amino acids joined together by a peptide bond. It may be appreciated that polypeptides can contain amino acids other than the 20 amino acids commonly referred to as the 20 naturally occurring amino acids. Also, polypeptides can include one or more amino acids, including the terminal amino acids, which are modified by any way known in the art (whether naturally or non-naturally). For purposes herein, polypeptides include, e.g., proteins, peptides, and/or protein fragments. "Analyzing the protein/peptide content" as defined in the present invention refers to the determination of the type or amount of protein/peptide in a tissue or cellular sample using the methods of the present invention.

In the context of the present invention, the term 'Matrix-assisted (laser) desorption/ionization' (MALDI), is a method of mass spectrometry that involves the use of an energy absorbing molecule, frequently called a matrix, for desorbing peptides/proteins intact from a probe surface. MALDI is an ionization technique that uses an energy absorbing matrix to create ions from molecules with minimal fragmentation. MALDI is a three-step process. First, the sample is mixed with a suitable matrix material and applied to a metal plate, second a pulsed energy beam (typically a laser) irradiates the sample, triggering ablation and desorption of the sample and the matrix material. Finally, the analyte molecules are ionized by being protonated (positive mode) or deprotonated (negative mode) in the hot plume of ablated gases, and can then be accelerated into whichever mass spectrometer is used to analyze them. Alternatively to classical MALDI methods, other types of mass spectrometry analysis methods may also be used, such as for example Matrix assisted SIMS (secondary ion mass spectrometry), in which a primary ion beam instead of a laser is used for desorption.

MALDI-MSI is a technique that allows for imaging of surfaces and has been shown to be quite versatile in its many applications to the analysis of biological samples, such as peptides and proteins. Typically, samples are coated with a matrix (often an organic acid) to facilitate ablation and ionization of compounds in the sample. This coating is typically done 'as dry as possible, in order to prevent delocalization of the analyte by lateral diffusion. The presence of this matrix is necessary to provide the required sensitivity and specificity to use laser desorption techniques in the analysis of biological material. The application of thin layers of matrix has special advantages, particularly when very high sensitivity is needed. MALDI-MSI may be used to generate images of samples in one or more m/z pictures, providing the capability for mapping the concentrations of specific molecules in X, Y coordinates of the original biological sample. A MALDI-MSI "image" is achieved by desorption and measurement of tissue Ions (proteins/peptides, lipids, glycans, or other ions) from focused regions, which is subsequently summed across the entire tissue field. Each "spot" is a piece of the composite picture resulting from the grid arrangement of the spots. In this way, a protein/peptide that is overexpressed or underexpressed can have the related MSI signal associated with the tissue region. In effect a region of the tissue that selectively expresses a discrete peptide will display an area of high expression that can be seen from the MS data. In certain embodiments, such images may be matched to a mirror tissue (such as an adjacent histologically stained tissue section) that is reviewed by a pathologist and provides him/her supplemental information to aid in diagnosis and staging/grading of a disease.

MALDI Mass Spectrometry Imaging (MALDI-MSI) uses the detection capability of mass spectrometry with the positional information of molecular histology, generating mass spectra correlated to known locations within a tissue. MALDI mass spectrometry imaging is able to reveal the distribution of a large range of analytes. This information can be used to determine the distribution of an analyte throughout a tissue or organism. Since its introduction by the team of Caprioli (Caprioli et al., 1997) Mass Spectrometry Imaging (MSI) has become a powerful and versatile tool for analyzing different classes of endogenous and exogenous molecules. In imaging mass spectrometric analysis, i.e. the acquisition of a mass spectrometric image, tissue sections are mass spectrometrically analyzed, usually with ionization by matrix-assisted laser desorption (MALDI). To this end, a thin tissue section is placed onto an electrically conductive microscope slide, a metal target plate, or a regular untreated microscope glass, as sample support. A thin layer of a matrix substance is then applied onto the tissue section by a suitable method not generating much lateral mixing of the tissue components, in such a way that finally the dried matrix substance layer contains the soluble peptides (and also other soluble substances) in an extracted form. The sample support is introduced into a mass spectrometer, and mass spectra of the individual image points are acquired.

Sample preparation is a critical step in MSI. Thereto, thin tissue (paraffin embedded) slices are mounted on the respective microscope slides and a suitable MALDI matrix is applied to the tissue either manually or automatically. Next, the microscope slide is inserted into a MALDI mass spectrometer. The mass spectrometer records the spatial distribution of molecular species such as peptides, proteins or small molecules.

In the present method, samples are provided as thin tissue sections of (formaldehyde-fixed), paraffin-embedded biological material. Embedding of tissue sample into paraffin blocks is a standard method for allowing very thin sections to be cut and mounted onto microscope slides for analysis. This technique is thus highly suitable for sample preparation for use in MALDI-MSI, which as discussed above works well with thin tissue slices for detection.

Formaldehyde (such as formalin) fixation is a fixation method used in the fields of histology, pathology, cell biology, . . . for the preservation of biological tissues from decay. Tissue fixation is a critical step in the preparation of histological sections, specifically to allow the preparation of thin sections. Formaldehyde is one of the most commonly used fixatives in histology and fixes tissue by cross-linking the proteins. Paraformaldehyde is also commonly used and depolymerizes to formalin when heated. Hence, in the context of the present invention, the term formaldehyde-fixed sample is meant to be a sample which is fixed using a (para)formaldehyde containing solution.

While the method of the present invention is particularly suitable for (formaldehyde-fixed), paraffin embedded biological material, the method could also be applied to (formaldehyde-fixed) tissue sections, including thin ones, which have not been paraffin embedded prior to sectioning, in as long as the sample consistency in itself allows for thin sectioning, or is thin enough on its own to allow for (whole mount) mass spec imaging analysis. In such instance, the method of the present invention comprises the following steps:

a) providing a (formaldehyde-fixed) biological sample;
b) thin sectioning said sample of step a) or directly depositing thin sample of step a on a suitable MALDI surface (such as glass, metal, metal coated glass, . . . );
c) applying a MALDI (matrix-assisted laser desorption ionization imaging) matrix to said samples of step b; and
d) performing a mass spectrometry analysis tuned for peptide analytes on said sample of step c).

Where the starting material is not a paraffin embedded sample, especially in cases where the sample is too thick for direct analysis as 'whole mount' (which would not require embedding at all), it should be selected such that it allows for thin sectioning of the samples using an appropriate sectioning device. For example, the sample may be embedded in an agarose-type of gel such as for sectioning on a vibratome. Alternatively, a cryotome may be used to section frozen tissue samples. A classical microtome on the other hand is typically used to section paraffin embedded samples.

The tissue sections can be cut to any suitable thickness for MALDI-MSI, and are typically cut to a thickness between about 5 to about 25 µm. It shall be clear that there is no principal restriction with regard to the section thickness. Sections below 5 µm can likewise be analysed, with the limit being the sectioning skills of the microtome operator, and sections up to 0.5 mm (and higher) will also work, as long as the mass spectrometer source geometry can accommodate these thicker samples. Hence, in the context of the present invention the term 'thin' is meant to be having a typical thickness anywhere between 1 to about 50 µm, such as between 1 to about 10 µm, between 10 to about 20 µm, between 20 to about 30 µm, between 30 to about 40 µm, or between 40 to about 50 µm. Similarly, the term 'thin sectioning' is meant to be the sectioning, slicing, cutting, . . . of a sample to obtain a thin slice/section, i.e. having a thickness anywhere between about 1 to about 50 µm.

MALDI detection methods using paraffin embedded samples, require the paraffin to be removed. Hence, the method encompasses a paraffin removal step. However, as discussed herein above, we discovered that during classical sample preparation steps, a lot of vital information is lost due to washing off of small (endogenous) peptides, as these are likely relatively freely and easily extractable from the section. Therefore, in the context of the present invention, it is essential that the hydrophilic steps within the deparaffinization method are kept as short as possible, in order not to wash out these peptides. Hence, the deparaffinization method is kept as short as possible, including a minimum number of steps: sufficient to efficiently remove the paraffin, but maximally reducing the removal of small peptides. It is evident for a person skilled in the art that the number and length of the different deparaffinization steps is dependent on the thickness of the tissue samples, i.e. the amount of paraffin in the sections. For example, for very thin slices (e.g. 2-10 µm), 2 deparaffinization steps each lasting for about 1-2 min will likely be sufficient, whereas for thicker slices (e.g. 10-50 µm), it is likely that 3-4 deparaffinization steps each lasting about 2-5 min is required.

Thereto, the present invention provides a method as defined herein wherein the deparaffinization step is performed by immersing the PE sample/section at room temperature 1-5 times in 100% xylene for about 1-5 min, followed by 1-5 washing steps in absolute (typically 95-96%) ethanol, each lasting about 1-5 min. While this specific example includes the use of xylene and ethanol, any MALDI-compatible deparaffinization solutions [e.g. biosafe alternatives for xylene (Rai et al., 2016)] may be used in the context of the present invention. It is however essential that these solutions contain as little water as possible (i.e. are substantially and/or essentially free from water), and that the different deparaffinization steps are kept as short as possible, in order not to lose too much of the peptide content from the samples.

A particularly suitable deparaffinization protocol for tissue sections of about 20 µm is as follows: immersing the sectioned PE samples at room temperature sequentially in:

100% xylene for about 3 min;
100% xylene for about 2 min;
absolute ethanol for about 2 min; and
absolute ethanol for about 1 min.

After the deparaffinization steps, any residual washing solution (e.g. ethanol) is allowed to evaporate from the sectioned samples, since remaining solution prior to matrix deposition may result in enhanced (peptide) analyte delocalization from the samples. When using absolute ethanol in the last deparaffinization step, it is sufficient to allow the samples to air dry, however, any other suitable method for (accelerated) drying the deparaffinized samples may also be used, such as for example vacuum drying in a dessicator or freeze-drying.

In classical MALDI-MSI methods, after drying the samples, an enzymatic digestion and/or antigen-retrieval step is performed. However, in the context of the present invention, it is essential that such steps are not performed, since these were found to extract/remove a large amount of peptides of which it was the object of the invention to be detected. Thereto, the methods of the present invention are characterized in that they do not comprise an enzymatic digestion step, nor an antigen-retrieval step. Contrary to the general understanding in the field, we found that these steps are not needed to allow detection of (endogenous) peptides. In contrast, using this newly developed method, we could even differentiate tumor sample from normal tissue based on their peptide profile. Until now, this has been very difficult, presumably due to the washing off of differentiating peptides during the processing steps of the samples, which resulted in the analyte concentration being reduced to below the sensitivity threshold of the peptide mass spectrometry employed. Hence, the present invention also provides a new method for diagnostic imaging as well as peptide biomarker identification, including for disease areas which are at present difficult to diagnose and/or stage.

Hence, in the methods of the present invention, after the drying step, the thin (usually microtome sectioned) and deparaffinized samples are directly coated with a MALDI matrix, without intermediate enzymatic digestion of antigen-retrieval steps.

A "matrix" or a "matrix liquid" refers to a material used in MALDI-MSI to prepare the sample analyte for analysis. This material absorbs energy from the laser and transfers the energy to the analyte to desorb, volatize, and ionize the analyte, thereby producing ions from the analyte that are then analyzed in the mass spectrometer to yield information about the analyte. In the context of the present invention, conventional MALDI matrices are used. Particularly, it is not required to include a (non-conventional) special reactive matrix, like 2,4-dinitrophenylhydrazine (DNPH). The term 'reactive matrix' is meant to be a matrix which promotes the liberation of aldehydes, i.e., the reversal of the (form) aldehyde crosslinking. Hence, in a particular embodiment, the method of the present invention does not comprise the use of a special 'reactive' matrix, typically used in reversing (form)aldehyde crosslinks.

Examples of such (conventional) matrix materials or matrix liquids include, but are not limited to sinapinic acid (SA) and derivatives thereof, such as alpha-cyano sinapinic acid; cinnamic acid and derivatives thereof, such as [alpha]-4-cyano hydroxyl cinnamic acid (CHCA); 2,5-dihydroxybenzoic acid (DHB); 3-hydroxypicolinic acid; dithranol and derivatives thereof. Alternative nanomaterial suitable for peptide analysis (see Lu et al., 2017) may also be suitably used within the context of the present invention. In a particular embodiment, reactive MALDI matrices such as 2,4-dinitrophenylhydrazine are not used in the methods of the invention.

Matrices have evolved to include small organic molecules and heavy metals that that can be applied to or mixed with the analyte. Specific examples include heavy metals (such as, but not limited to, gadolinium, cobalt and bismuth) and glycerol. The most often used matrices absorb light at 337 [lambda], the wavelength of a nitrogen laser, and thereby facilitate desorption and ionization of adjacent biological materials. Ions of the same charge acquire a similar kinetic energy; however, their velocity in the ion chamber depends on their respective masses. In a typical time-of-flight (TOF) analyzer, the ion time of travel to an anode is measured, precisely by the detector and is recorded as a mass/charge (m/z) spectrum with peaks representing proteins/peptides in the sample. It is evident that mass spectrometry systems in which a suitable source (typically MALDI or SIMS) is interfaced with other analyzers or analyzer combinations (in so-called tandem MS systems), suitable for peptide (tandem) mass spectrometry, can also be used, provided the overall sensitivity of the complete system is adequate. Examples are quadrupoles, ion traps, orbitraps, or other Fourier Transform MS instruments (Wysocki et al., 2005). Based on instrument calibration of standard samples, the acquired m/z values are converted to mass values, which can be used for direct database aided analysis, using e.g., UniProt (or other protein sequence) databases with Mascot(c), and Blast(c) software or similar algorithms, or using spectral libraries (especially for high resolution systems) or for de novo sequencing.

In a specific embodiment, in the context of the present invention, the MALDI matrix is supplemented with an additive to direct analyte ionization and desorption, such as $Li^+$-salts. Because of its superior electronegativity, $Li^+$ has a tendency to form cation adducts with peptide (and other biomolecular) analytes, which is higher than that of $H^+$, $Na^+$, $K^+$ or other potential adduct forming cations. This way some peptides, the ion signals of which are typically 'diluted' over $H^+$, $Na^+$ and $K^+$ peaks, are typically all concentrated in a single $Li^+$-peak, hence dramatically increasing the detection sensitivity. Moreover, $Li^+$-peptides tend to yield tandem MS fragmentation spectra which are richer in product ion peaks, which helps peptide sequence elucidation.

The matrix may be prepared typically at a near saturation concentration (although concentrations of about 10 mM often also work well). This concentration may be modified depending on the circumstances presented. For example, a DHB preparation can be made by dissolving 50 mg/ml dihydroxybenzoic acid in 0.2% TFA (trifluoroacetic acid). As for the deparaffinization steps, also the application of the MALDI matrix is such that it reduces the risk of losing peptides. Thereto, a minimum number of matrix layers, each as thinly as possible is applied to the samples. In order not to promote lateral diffusion (thus delocalization) of the (water soluble) peptide analytes on the tissue section surface, the MALDI matrix deposition is performed following the state-of-the-art techniques, such as pneumatic spraying, nebulization, vaporization/sublimation, acoustic nanodroplet deposition, etc.

This is no trivial task because, the soluble analytes (peptides) must be allowed to get extracted from the tissue section (as efficiently as possible) to get co-crystallized with the matrix in a favorable ratio analyte/matrix/impurities, all without causing peptide delocalization from its original position in the sample. Some impurities greatly reduce the ionization yield.

Further of high relevance within the context of the present invention, is that the mass spectrometry device is tuned for detecting peptide analytes. A person skilled in the art is well aware of the required settings for each individual mass spectrometry device to allow specific detection of peptide analytes. In general, this can be achieved by:

striking the test specimen with a laser beam such that a predetermined first laser spot on the test specimen releases first sample molecules;

measuring the molecular atomic mass of the released first sample molecules over a range of atomic masses;

moving the test specimen relative to the laser beam a predetermined linear distance functionally related to a size of the predetermined first laser spot;

thereafter striking the test specimen with the laser beam such that a predetermined second laser spot on the test specimen releases second sample molecules;

measuring the molecular atomic mass of the released second sample molecules over a range of atomic masses; and analyzing an atomic mass window of interest within the range of atomic masses to determine the spacial arrangement of specific molecules within the sample.

The variety of mass spectrometry instruments and methods suitable for peptide analyses is reviewed by Wysocki et al. (2005), of which the content thereof, is herein incorporated by reference.

EXAMPLES

Example 1

Neuropeptide Imaging in FFPE Tissues of Model Animal Species

Material and Methods

Animals

American cockroaches (*Periplaneta americana* L.) were taken from a stock colony maintained under standard conditions in the laboratory (Matthews et al., 1973), and provided with dry dog food, oatmeal and water ad libitum. For this study, all insect specimens selected were of the same developmental stage and sex.

Tissue Collection and Fixation

Retrocerebral complexes, i.e. corpora cardiaca (CC) and corpora allata (CA) of adult female cockroaches *Periplaneta americana* retrocerebral complexes were dissected, while the tissue was immersed in 4% paraformaldehyde (i.e., 10% formalin). Tissues were left in fixative over night, after which they were conventionally dehydrated and paraffin embedded, exactly as we described earlier (Verhaert et al., 1986). In fact, all thus formalin fixed paraffin embedded (FFPE) tissues used were actually 'leftovers' from the very same study published in 1986.

Tissue Sectioning

More than 30 years after paraffin embedding, the cockroach neuroendocrine tissues were histologically sectioned at 20 µm thickness on a microtome (Leica Reichert-Jung 2040 Autocut).

Sections were transferred to a drop of distilled water deposited onto indium tin oxide (ITO) coated microscope glasses, which had been rinsed with ethanol and air dried immediately before. The slides were put on a hotplate (50 C) where the paraffin sections stretched and were allowed to dry for, at least, 30 minutes.

Further Tissue Preparation for MALDI-MSI

Microscope slides containing the tissues were deparaffinized and 'hydrated' by consecutively immersing them at RT (room temperature) in xylene and ethanol baths under a fume hood (Table 1).

TABLE 1

Deparaffinization scheme of 20 µm tissue sections mounted on ITO coated microscope glasses.

| Name | Bath content | Immersion time |
|---|---|---|
| Xyl-1 | 100% xylene | 3 min |
| Xyl-2 | 100% xylene | 2 min |
| EtOH-1 | 96% ethanol | 2 min |
| EtOH-2 | 96% ethanol | 1 min |

After deparaffinization and prior to MALDI matrix deposition, the microscope slides were allowed to air dry (fume hood), after which the position of the tissue sections was marked with a permanent marker at the back of the microscope slide. This to assist later localization of the relevant sections with the optical camera mounted onto the source of the mass spectrometer.

MALDI Matrix Preparation and Deposition

Dihydroxybenzoic acid solution (DHB, 50 mg/ml in 0.2% TFA) was freshly prepared on the day of the mass spectrometry analysis. The slides were subsequently coated using a TM Sprayer unit (HTX Technologies, Chapel Hill, N.C., USA) with the following settings: spraying tip held at 70 C; 3 deposition layers (i.e. 3 passes of nozzle over tissue).

Mass Spectrometry Imaging

Accurate mass measurements were performed with an Orbitrap Elite mass spectrometer (Thermo Fisher Scientific, Bremen, Germany) coupled to an intermediate pressure MALDI source based on a dual ion funnel geometry (Spectroglyph LLC, Kennewick, Wash., USA). To enable synchronisation with any $MS^n$ event (ion trap or Orbitrap) stage motion was synchronized with the ion trap injection. All Orbitrap spectra are acquired at a mass nominal mass resolution of 240,000 FWHM using a 250 ms injection time. The laser was operated at 1 kHz, a pulse energy of ~1.5 µJ and focussed to a ~20 µm spot. Mass accuracies are typically less than 1.5 ppm after single point internal calibration. Visualisation of data was achieved by converting the raw data into a Matlab readable format and using in-house developed Matlab tools.

High-throughput measurements were performed with a Bruker rapifleX MALDI Tissuetyper™ TOF mass spectrometer operating in reflectron mode, with a laser raster size of 40 $µm^2$ and a stage motion (i.e., pixel size) of 50 $µm^2$. At each raster position, 200 laser shots were summed to generate a representative spectrum for each pixel, with the digitizer sampling rate at 1.25 GS/s. Visualisation of the data was achieved using flexImaging 4.0 software (Bruker Daltonics, Billerica, Mass., USA).

Results

All peptides which we previously published that could be imaged in freshly prepared (whole mount) cockroach neurohaemal tissue could be detected (with similar ppm accuracy) and imaged from the 20 µm thick sections of the >30 years old paraffin embedded material. Moreover, additional peptides not reported in Verhaert et al. (2010), but previously described in the literature as true cockroach neuropeptides (e.g. proctolin) could be imaged in the FFPE tissue section (peptide sequence and masses list see Table 2). In addition, also previously undescribed peptides could be imaged, and partial sequence information could be deduced from on-tissue tandem MS analyses of the respective precursor ions.

TABLE 2

Peptide sequences and their corresponding ion masses imaged and MS/MS identified on FFPE tissue sections from cockroach neurohaemal organs.

| Sequence | [trivial name] | m.i. mass [M + H] | (→ derived masses) |
|---|---|---|---|
| RYLPT | [proctolin] | 649.36679 | |
| SPPFAPRLamide | [Pea-PK-II] | 883.514848 | |
| pQVNFSPNWamide | [Pea-CAH-I] | 973.452642 | (→ 995.434586 [M + Na], 1011.408524 [M + K]) |
| pQLTFTPNWamide | [Pea-CAH-II] | 988.488693 | (→ 1010.470637 [M + Na], 1026.444575 [M + K]) |
| LVPFRPRLamide | [Pea-PK-III] | 996.646531 | |
| HTAGFIPRLamide | [PEA-PK-I] | 1010.589410 | |
| pQDVDHVFLRFamide | [Pea-LMS] | 1257.637482 | |
| FDDY(SO$_3$)GHMRFamide | [<Pea-SK] | 1266.466653 | (→ 1186.509839 [M + H-SO$_3$]) |

TABLE 2-continued

Peptide sequences and their corresponding ion masses imaged and MS/MS identified on FFPE tissue sections from cockroach neurohaemal organs.

| Sequence | [trivial name] | m.i. mass [M + H] | (→ derived masses) |
|---|---|---|---|
| pQSDDY(SO₃)GHMRFamide | [Pea-LSK-II] | 1317.462296 | (→ 1237.505482 {M + H-SO₃]) |
| pQTFQYSRGWTNamide | [corazonin] | 1369.628374 | |
| EQFDDY(SO₃)GHMRFamide | [Pea-SK] | 1523.567824 | (→ 1443.611009 [M + H-SO₃]) |
| DHLPHDVYSPRLamide | [Pea-PK-IV] | 1447.744071 | |
| SESEVPGMWFGPRLamide | [Pea-PK-VI] | 1590.773324 | |
| GGGGSGETSGMWFGPRLamide | [Pea-PK-V] | 1651.764550 | |

Example 2

Endogenous Peptide Imaging in FFPE Tissues of Human Colon (Carcinoids and Normal Mucosa)

Material And Methods

Tissue Selection

A small microarray was composed from human FFPE colon tissues from the biobank of the General Hospital at Herentals (Belgium). Five tissue cores consisted of colon carcinoids (from 5 different patients), two cores represented 'healthy' (not cancerous) colon mucosa.

Tissue Sectioning

The tissue microarray was sectioned at 10 μm thickness using a microtome both on ITO coated as well as regular microscope glass slides.

Further Tissue Preparation for MALDI-MSI

Deparaffinization was accomplished in 2 consecutive baths of 100% xylene (3 min and 2 min respectively), and 2 baths of 100% ethanol (2 min and 1 min).

MALDI Matrix Preparation and Deposition

DHB (2,5 dihydroxybenzoic acid, 50 mg/ml in 0.2% TFA) solution was freshly prepared on the day of the mass spectrometry analysis. The slides were subsequently coated using a TM Sprayer unit (HTX Technologies, Chapel Hill, N.C., USA) with the following settings: spraying tip held at 70 C; 3 deposition layers (i.e. 3 passes of nozzle over tissue).

Mass Spectrometry Imaging

Tissue sections prepared as above were analysed by MSI in a 7T MALDI Qq FTICR mass spectrometer (solariX XR, Bruker), as well as on a MALDI TOF (rapifleX, Bruker), both tuned for peptide ions between m/z 500 and 2000.

Immunohistochemical Classification

Three antisera to known tumor markers were employed in immunoperoxidase labelings: chromogranin A, synaptophysin, and cytokeratin.

Results

The majority of the ion signals observed on the tissue cores were equally spread over the 7 samples. However, of several ions which show a peptide like isotopic pattern, the mass spectral image was found to correlate with the carcinoid or healthy nature of the sample. The carcinoid nature of 5 of the 7 cores of the tissue microarray was confirmed by the immunohistochemical classification, which showed a clear overexpression of the tumor markers compared to the healthy tissue. Interestingly, whereas the immunohistochemical stainings do not allow to distinguish between aggressively growing tumors and less malignant ones, the intensities of certain peptide mass spec images seem to correlate with such features, as confirmed by histopathological experts.

Figure 2:
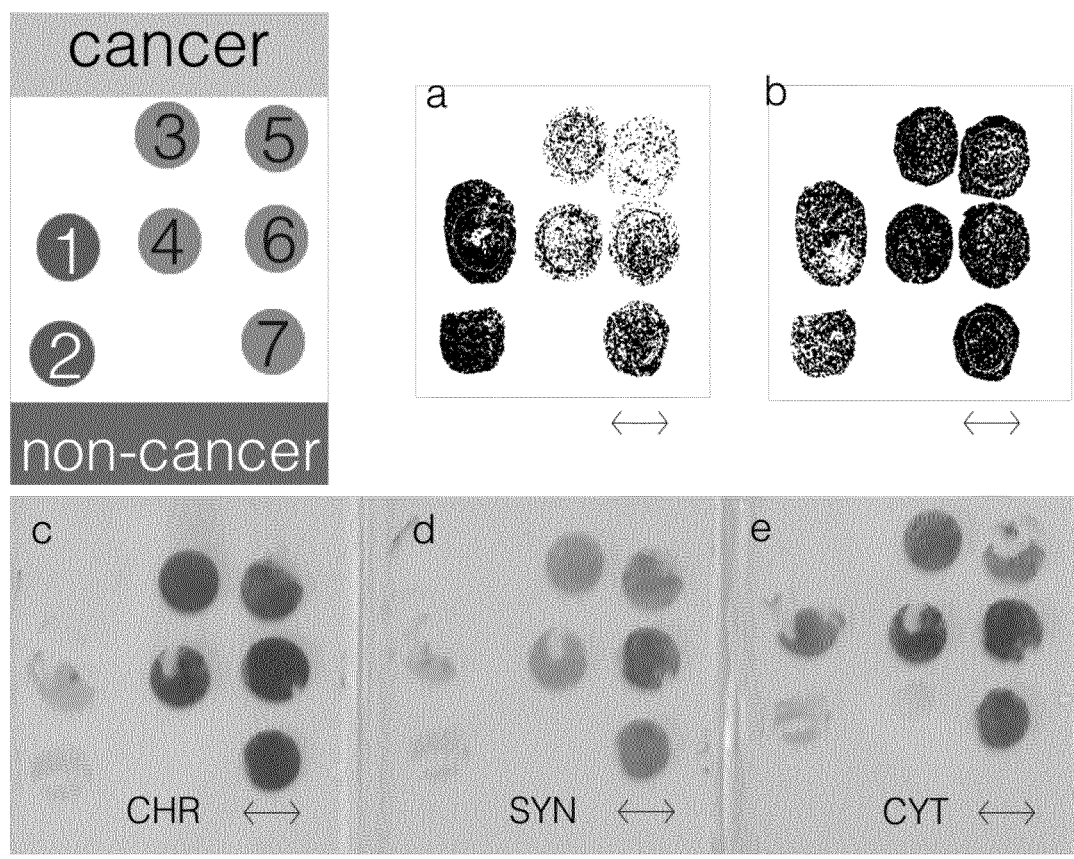
FIG. 2: Human colon tissue microarray (TMA) consisting of 2 normal ('healthy') colon mucosa (tissue cores #1 and 2), and 5 colon carcinoids (from 5 patients; tissue cores #3-7). Design of array is shown in top left corner. (a) Mass spectrometry image of peptide ions showing increased signal in carcinoid (cores #3-7); (b) mass spectrometry image of peptide ions with increased signal intensity over healthy tissue (cores #1-2). (a) and (b) show different peptide ion m/z images of same histological section through TMA [peak intensity scale is from black (low intensity) to white (high intensity)]. (c)-(d) show light microscopic immunohistochemical images of anti-chromogranin A antibodies (CHR), anti-synaptophysin antibodies (SYN) and anti-cytokeratin antibodies (CYT) [immunoperoxidase labeling resulting in dark immunopositive stainings]. Three consecutive sections through the TMA, adjacent to section displayed in (a) and (b) were separately immunostained. Double arrow scale bar=4 mm.

Selected results of these analyses can be found in FIG. 2.

Example 3

Neuropeptide Imaging in FFPE Tissues of Human Pituitary Gland

Material and Methods

Tissue Selection

Human pituitary FFPE blocks were obtained from the university hospital biobank at Leuven (Belgium). They contained pituitary tissues surgically resected (between 3 and 7 years ago) from 5 different patients with a tumor in the adenohypophysis, and fixed in formaldehyde and embedded in paraffin using the standard hospital protocols. The tissue blocks were especially selected for the presence, besides the resected adenohypophysis (anterior pituitary) matter, of adjacent neurohypophysis (posterior pituitary) tissue.

Tissue Sectioning

Tissue blocks were sectioned at 5 μm thickness using a microtome both on ITO coated as well as regular microscope glass slides.

Further Tissue Preparation for MALDI-MSI

Full deparaffinization was accomplished in consecutive baths of 100% xylene (2×2 min), and one bath of 100% ethanol (1×2 min).

MALDI Matrix Preparation and Deposition

DNB (2,5 dihydroxybenzoic acid) matrix was applied to the tissue sections in an automated system with sublimation (2 μm matrix thickness; Shimadzu IMLayer). Prior to insertion in the MS instrument, the matrix was recrystallized on the tissue (1.5 min in a closed chamber at 75° C. in the presence of a paper tissue with 500 μL MeOH:H₂O 5:1000).

Mass Spectrometry Imaging

Tissue sections prepared as above were analysed by MSI in an integrated microscope ion trap-TOF hybrid mass spectrometer (iMScope TRIO, Shimadzu). Mass range was set from m/z 500 to 1700. Source voltage was 3.5 kV; detector voltage was set at 2.0 kV. Ions were recorded in positive ionization mode. Spectra were recorded at 5 μm spatial resolution. One hundred laser shots were accumulated per pixel (at a 1000 Hz laser repetition rate), i.e. 10 pixel/s data acquisition rate.

Collision induced dissociation MS/MS was performed on tissue of selected precursor ions for primary structure confirmation.

Results

In particular, ions representing 2 neuropeptides were found to be prominently present in, especially the neurohypophysis part of the tissues. All 5 different samples exhibited clear images of 1084.445 and 1007.446, i.e., the protonated forms of vasopressin and oxytocin respectively. Both peptides were thus found to be present in their fully modified structure, i.e. including the aminoterminal disulfide bridge between Cys1 and Cys6, and the C-terminal amide. In addition, both vasopressin, and particularly oxytocin were also detected as sodium adduct (at 1106.426 and 1029.426).

MSMS analysis confirmed the primary structure of the peptides. Indeed, in particular the $b_6$- and $y_3$-fragment ions aminoterminally from both peptides' Pro7 residue were very prominent in the tandem MS spectra.

Figure 3:
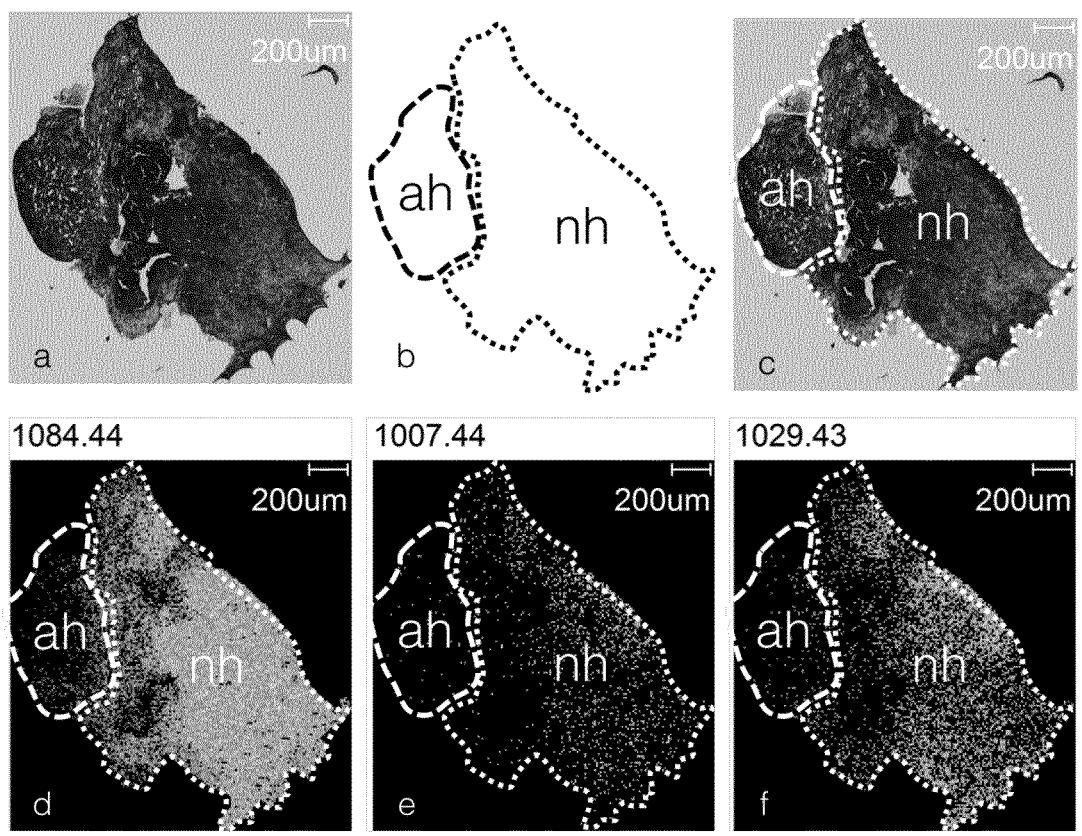
FIG. 3: Cross section through human pituitary gland:
(a) Light optical image of tissue section
(b) Histological annotation (by pathologist) of adenohypophysis (ah) and neurohypophysis (nh) part
(c) Overlay of (a) and (b)
(d) Mass spectrometry image of ion m/z 1084.44, corresponding to vasopressin $[M+H]^+$ monoisotopic mass
(e) Mass spectrometry image of ion m/z 1007.44, corresponding to oxytocin $[M+H]^+$ monoisotopic mass
(f) Mass spectrometry image of ion m/z 1029.43, corresponding to oxytocin $[M+Na]^+$ monoisotopic mass

Selected results of these analyses can be found in tables 3 and 4, and FIG. 3.

TABLE 3

Peptide ions observed by mass spec imaging on human FFPE neurohypophysis. Comparison with calculated masses of known human neuropeptides oxytocin and vasopressin.

| observed m/z | neuropeptide | interpretation | calculated mass |
| --- | --- | --- | --- |
| 1007.445 | oxytocin | $[M + H]^+$ | 1007.444 |
| 1029.426 | oxytocin | $[M + Na]^+$ | 1029.426 |
| 1084.445 | vasopressin | $[M + H]^+$ | 1084.445 |
| 1096.445 | vasopressin | $[M + C + H]^+$(Shiff base) | 1096.445 |
| 1106.426 | vasopressin | $[M + Na]^+$ | 1106.426 |

TABLE 4

Major characteristic fragment ions observed after on-tissue MSMS of precursor ions 1007 and 1084.

| Precursor m/z | observed m/z | fragment ion | calculated mass |
| --- | --- | --- | --- |
| 1007 | 723.257 | $y_3$ | 723.274 |
| 1084 | 775.244 | $y_3$ | 755.259 |
| | 328.208 | $b_6$ | 328.209 |

REFERENCES

Caprioli, R. J., et al. (1997) Molecular imaging of biological samples: localization of peptides and proteins using MALDI-TOF MS. Anal Chem. 69:4751-4760.

Chaurand, P., et al. (2008) Imaging mass spectrometry of intact proteins from alcohol-preserved tissue specimens: bypassing formalin fixation. Journal of Proteome Research 7: 3543-3555.

Gustafsson, O. J. R., et al. (2015) Proteomic developments in the analysis of formalin-fixed tissue. Biochim. Biophys. Acta—Proteins and Proteomics 1854: 559-580.

Lemaire, R., et al. (2007) Direct analysis and MALDI Imaging of Formalin-Fixed Paraffin-Embedded Tissue Sections—Journal of Proteome Research 6, 1295-1305.

Lu, M., et al. (2017) Nanomaterials as assisted matrix of laser desorption/ionization time-of-flight mass spectrometry for the analysis of small molecules. Nanomaterials 7: 87 doi: 10.3390/nano7040087.

Matthews, J. R.; Downer, R. G. H. Hyperglycemia induced by anesthesia in the American cockroach, *Periplaneta americana* L. Can. J. Zool. 1973, 51: 395-397.

Predel, R.; Gaede, G. Peptidomics of neurohemal organs from species of the cockroach family Blattidae: how do neuropeptides of closely related species differ? *Peptides* 2005, 26: 3-9.

Quesada-Calvo, F., et al. (2015) Comparison of two FFPE preparation methods using label-free shotgun proteomics: Application to tissues of diverticulitis patients. J. Proteomics 112: 250-261.

Rai, R., et al. (2016) Biosafe substitutes for xylene, Int. J. Inform. Res. Rev. 3: 2529-2532).

Shaw, C.; Verhaert, P. D. E. M. Peptidomics and Biology, Two disciplines driving each other. In "*Peptidomics: Methods and Applications*", Soloviev, M.; Shaw, C.; Andrén, P. (Eds.), John Wiley & Sons: 2007, pp. 389-396 [doi: 10.1002/9780470196502.ch17].

Verhaert, P.; De Loof. A.; Huybrechts, R.; Delang, I.; Theunis, W.; Clottens, F.; Schoofs, L.; Swinnen, K.; Vandesande, F. A new alternative for simultaneous immunohistochemical screening of 96 hybridoma clones for tissue-specific antibody productions selects a monoclonal antibody to insect corpus cardiacum. *Journal of Neuroscience Methods* 1986, 17: 261-268.

Verhaert, P. D. E. M.; Pinkse, M. H.; Strupat, K.; Conaway, M. P. Imaging of Similar Mass Neuropeptides in Neuronal Tissue by Enhanced Resolution MALDI MS with an Ion Trap—Orbitrap™ Hybrid Instrument. In "*Mass Spectrometry Imaging*". Rubakhin, S. S.; Sweedler, J. V. (Eds.), Humana Press: 2010, pp. 433-449.

Wiśniewski, J. R. (2013) Proteomic Sample Preparation from Formalin Fixed and Paraffin Embedded Tissue. J. Vis. Exp. 79, e50589, doi:10.3791/50589 (2013).

Wysocki, V. H.; Resing, K. A.; Zhang, Q.; Cheng, G. Mass spectrometry of peptides and proteins. Methods 2005, 35: 211-222.

The invention claimed is:

1. A method for imaging peptides in a formaldehyde-fixed paraffin-embedded biological sample, the method comprising:
    (a) providing a formaldehyde-fixed paraffin-embedded biological sample;
    (b) sectioning the sample of (a);
    (c) deparaffinizing the sectioned sample of (b);
    (d) air drying the sectioned sample of (c);
    (e) applying a MALDI (matrix-assisted laser desorption ionization imaging) matrix to the air-dried samples of (d), the MALDI matrix being selected from the group consisting of sinapinic acid, alpha-cyano sinapinic acid, cinnamic acid, alpha-4-cyano hydroxyl cinnamic acid, 2,5-dihydroxybenzoic acid, 3-hydroxypicolinic acid, dithranol, derivatives thereof and combinations thereof; and
    (f) performing a mass spectrometry analysis tuned for peptide analytes on the sample of (e);
wherein the method does not comprise enzymatic digestion, and wherein the method does not comprise antigen-retrieval, and wherein the method does not include use of a reactive MALDI matrix comprising 2,4-dinitrophenylhydrazine.

2. The method according to claim 1, wherein (c) is performed by immersing the paraffin-embedded sample 1-5 times in 100% xylene for about 1-5 min, followed by washing 1-5 times in absolute ethanol, each washing lasting about 1-5 min.

3. The method according to claim 1, wherein (c) is performed by immersing the sectioned samples of (b) sequentially in:
(1) 100% xylene for about 3 min;
(2) 100% xylene for about 2 min;
(3) absolute ethanol for about 2 min; and
(4) absolute ethanol for about 1 min.

4. The method according to claim 1, wherein the MALDI matrix further comprises an additive to direct analyte ionization and desorption.

5. The method according to claim 1, wherein the mass spectrometry analysis is tuned for peptides.

6. The method according to claim 4, where the additive to direct analyte ionization and desorption is a $Li^+$ salt.

7. The method according to claim 1, wherein the MALDI matrix is a MALDI matrix that does not promote liberation of aldehydes through reversal of aldehyde crosslinking or formaldehyde crosslinking.

\* \* \* \* \*